(12) United States Patent
Taghipour et al.

(10) Patent No.: US 6,500,346 B1
(45) Date of Patent: Dec. 31, 2002

(54) FLUID TREATMENT DEVICE AND METHOD FOR TREATMENT OF FLUID

(75) Inventors: Fariborz Taghipour, London (CA); Yuri Lawryshyn, Komoka (CA); David A. Olson, London (CA); Zhang Tan, Mississauga (CA)

(73) Assignee: Trojan Technologies, Inc. (CA)

( * ) Notice: Subject to any disclaimer, the term of this patent is extended or adjusted under 35 U.S.C. 154(b) by 3 days.

(21) Appl. No.: 09/676,082

(22) Filed: Oct. 2, 2000

Related U.S. Application Data (60) Provisional application No. 60/157,009, filed on Oct. 1, 1999.

(51) Int. Cl.[7] .............................. C02F 1/30; C02F 1/32; B01J 19/12
(52) U.S. Cl. ..................... 210/748; 210/542; 250/438
(58) Field of Search ........................... 210/748, 542; 422/22, 24, 186.3; 250/435, 436, 438

(56) References Cited

U.S. PATENT DOCUMENTS

| | | | |
|---|---|---|---|
| 4,179,616 A | * | 12/1979 | Coviello et al. |
| 4,367,410 A | | 1/1983 | Wood |
| 4,471,225 A | * | 9/1984 | Hillman |
| 4,503,013 A | * | 3/1985 | Lowther |
| 4,661,264 A | * | 4/1987 | Goudy, Jr. |
| 4,766,321 A | * | 8/1988 | Lew et al. |
| 4,897,246 A | * | 1/1990 | Peterson |
| 4,990,311 A | * | 2/1991 | Hirai et al. |
| 5,124,131 A | * | 6/1992 | Wekhof |
| 5,151,174 A | * | 9/1992 | Wiesmann |
| 5,200,156 A | * | 4/1993 | Wedekamp |
| 5,208,461 A | * | 5/1993 | Tipton |
| 5,503,800 A | | 4/1996 | Free |
| 5,505,912 A | * | 4/1996 | Hallett |
| 5,874,740 A | | 2/1999 | Ishiyama |

FOREIGN PATENT DOCUMENTS

| | | |
|---|---|---|
| EP | 0 317 735 | 5/1989 |
| GB | 1584385 | 2/1981 |
| WO | WO 93/15830 | * 8/1993 |

* cited by examiner

Primary Examiner—David A. Simmons
Assistant Examiner—Fred Prince
(74) Attorney, Agent, or Firm—Katten Muchin Zavis Rosenman (57) ABSTRACT

A fluid treatment device, particularly useful for ultraviolet radiation treatment of fluids such as water. The device comprises a housing for receiving a flow of fluid. The housing has a fluid inlet, a fluid outlet, a fluid treatment zone disposed between the fluid inlet and the fluid outlet and at least one radiation source having a longitudinal axis disposed in the fluid treatment zone substantially transverse to a direction of the flow of fluid through the housing. The fluid inlet, the fluid outlet and the fluid treatment zone are arranged substantially collinearly with respect to one another. The fluid inlet has a first opening having: (i) a cross-sectional area less than a cross-sectional area of the fluid treatment zone, and (ii) a largest diameter substantially parallel to the longitudinal axis of the at least one radiation source assembly.

56 Claims, 7 Drawing Sheets

FLUID TREATMENT DEVICE AND METHOD FOR TREATMENT OF FLUID

This application claims benefit under 35 USC §119(e) to U.S. provisional application No. 60/157,009, filed Oct. 1, 1999.

BACKGROUND OF THE INVENTION

1. Field of the Invention

The present invention relates to a fluid treatment device. More particularly, in its preferred embodiment, the present invention relates to an ultraviolet radiation water treatment device.

2. Description of the Prior Art

Fluid treatment devices and systems are known. For example, U.S. Pat. Nos. 4,482,809, 4,872,980, 5,006,244 and 5,590,390 (all assigned to the assignee of the present invention) all describe gravity fed fluid treatment systems which employ ultraviolet (UV) radiation to inactivate microorganisms present in the fluid.

The devices and systems described in the '809, '980 and '244 patents generally include several UV lamps each of which are mounted within sleeves extending between two support arms of the frames. The frames are immersed into the fluid to be treated which is then irradiated as required. The amount of radiation to which the fluid is exposed is determined by the proximity of the fluid to the lamps. One or more UV sensors may be employed to monitor the UV output of the lamps and the fluid level is typically controlled, to some extent, downstream of the treatment device by means of level gates or the like. Since, at higher flow rates, accurate fluid level control is difficult to achieve in gravity fed systems, fluctuations in fluid level are inevitable. Such fluctuations could lead to non-uniform irradiation in the treated fluid.

However, disadvantages exist with the above-described systems. Depending on the quality of the fluid which is being treated, the sleeves surrounding the UV lamps periodically become fouled with foreign materials, inhibiting their ability to transmit UV radiation to the fluid. When fouled, at intervals which may be determined from historical operating data or by the measurements from the UV sensors, the sleeves must be manually cleaned to remove the fouling materials. Regardless of whether the UV lamp frames are employed in an open, channel-like system or a closed system, cleaning of the sleeves is impractical.

In open, channel-like systems, the modules comprising the sleeves are usually removed from the channel and immersed in a separate tank containing a suitable cleaning fluid. In closed systems, the device must be shut down and the sleeves are thereafter cleaned by charging with a suitable cleaning fluid or by removal of the lamps in the manner described for the open, channel-like systems. In either type of system, the operator must accept significant downtime of the system and/or invest significant additional capital to have in place sufficient redundant systems with appropriate control systems to divert the flow of fluid from the systems being cleaned.

The system described in the '390 patent is a significant advance in the art in that it obviates a number of disadvantages deriving from the devices and systems '809, '980 and '244 patents. Unfortunately, the system described in the '390 patent is ideally suited for use in an open, channel-like system and is not readily adaptable to be used in a completely closed system where the flow of fluid is fed under pressure in a pipe.

Closed fluid treatment devices are known—see, for example, U.S. Pat. No. 5,504,335 (assigned to the assignee of the present invention). The '335 patent teaches a closed fluid treatment device comprising a housing for receiving a flow of fluid. The housing comprises a fluid inlet, a fluid outlet, a fluid treatment zone disposed between the fluid inlet and the fluid outlet, and at least one radiation source module disposed in the fluid treatment zone. The fluid inlet, the fluid outlet and the fluid treatment zone are in a collinear relationship with respect to one another. The at least one radiation source module comprises a radiation source sealably connected to a leg which is sealably mounted to the housing. The radiation source is disposed substantially parallel to the flow of fluid. The radiation source module is removable through an aperture provided in the housing intermediate to fluid inlet and the fluid outlet thereby obviating the need to physically remove the device for service of the radiation source. A disadvantage with this kind of closed fluid treatment device is that the seal between the radiation source module and the housing must be broken each time the former is to be serviced. This confers additional cost and complexity to the servicing needs of the device.

Figure 1:
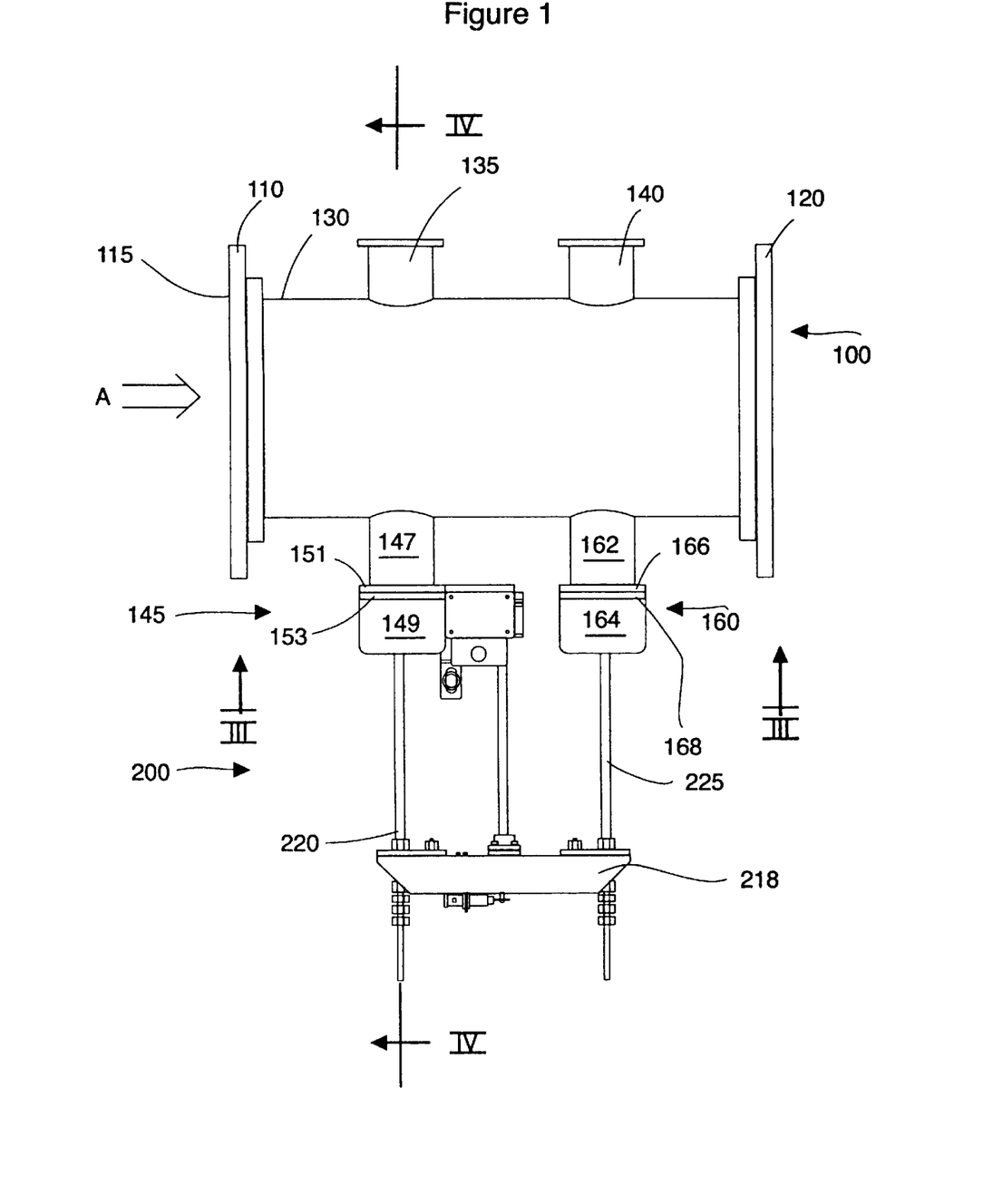
FIG. 1 illustrates a top plan view of a preferred embodiment of the present fluid treatment device.

Further, FIG. 1 of the '335 patent teaches a conventional closed fluid treatment device in which the inlet, outlet and fluid treatment zone are not in a collinear relationship with respect to one another. In the FIG. 1 embodiment, the lamp end connections extend out of the housing.

It would be desirable to have a fluid treatment device which can be readily adapted to treat a flow of fluid fed under pressure in a pipe or like enclosure. It would be further desirable if such a device was relatively easy to clean or keep clean during use. It would be further desirable if the radiation source in the device could be serviced while avoiding the problems associated with servicing the radiation source in the device taught in the '335 patent.

SUMMARY OF THE INVENTION

It is an object of the present invention to provide a novel fluid treatment device which obviates or mitigates at least one of the disadvantages of the prior art.

Accordingly, in one of its aspects, the present invention provides a fluid treatment device comprising a housing for receiving a flow of fluid, the housing comprising a fluid inlet, a fluid outlet, a fluid treatment zone disposed between the fluid inlet and the fluid outlet, and at least one radiation source having a longitudinal axis disposed in the fluid treatment zone substantially transverse to a direction of the flow of fluid through the housing;

the fluid inlet, the fluid outlet and the fluid treatment zone arranged substantially collinearly with respect to one another,     the fluid inlet comprising a first opening having: (i) a cross-sectional area less than a cross-sectional area of the fluid treatment zone, and (ii) a largest diameter substantially parallel to the longitudinal axis of the at least one radiation source.

In another of its aspects, the present invention provides a fluid treatment device comprising a housing for receiving a flow of fluid, the housing comprising a fluid inlet, a fluid outlet, a fluid treatment zone disposed between the fluid inlet and the fluid outlet, and at least one radiation source having an arc length and a longitudinal axis disposed in the fluid treatment zone substantially transverse to a direction of the flow of fluid through the housing;

the fluid inlet, the fluid outlet and the fluid treatment zone arranged substantially collinearly with respect to one another;

the fluid inlet comprising a first opening having: (i) a cross-sectional area less than a cross-sectional area of the fluid treatment zone, and (ii) a diameter less than the arc length of the at least one radiation source.

Thus, the present fluid treatment device and method relate to a closed system for treatment of a fluid. As used throughout this specification, the term "closed system", in relation to treatment of a fluid, is intended to encompass a system in which the flow of fluid is pressurized and substantially completely contained in an enclosure throughout treatment. Thus, open, channel-like systems are outside the scope of the present invention since, in the operation of such systems the level of water in the channel and/or treatment zone can vary. The source of pressurization of the flow of fluid is not particularly restricted. For example, the pressure can be generated by a pump or by the action of gravity.

Ideally, the present fluid treatment device and method may be used "in-line" in conventional water piping. Depending on the particular application, the piping can be up to 4 in. diameter for domestic applications, or 1 ft. to 3 ft. diameter or more for municipal applications.

BRIEF DESCRIPTION OF THE DRAWINGS

Embodiments of the present invention will be described with reference to the accompanying drawings, in which.

DETAILED DESCRIPTION OF THE PREFERRED EMBODIMENTS

With reference to FIGS. 1–4, there is illustrated a fluid treatment device 100. Fluid treatment device 100 comprises an inlet flange 110 and an outlet flange 120. Disposed between inlet flange 110 and outlet flange 120 is a housing 130.

Attached to inlet flange 110 is an inlet plate 115. A more detailed discussion of inlet plate 115 will be provided hereinbelow. Disposed in housing 130 are a pair of recesses 135,140. Preferably, housing 130 is constructed of stainless steel as are recesses 135,140, the latter being sealingly welded to housing 130.

Disposed opposite recess 135 is a recess 145. Disposed opposite recess 140 is a recess 160.

Recess 145 comprises a tubular section 147 which is connected to an end cap 149 via a first plate 151 and a second plate 153. The fluid tight arrangement of recess 145 will be described in more detail hereinbelow. Recess 160 comprises a tubular section 162 which is connected to an end cap 164 via a first plate 166 and a second plate 168.

Fluid treatment device 100 further comprises a cleaning device 200. Cleaning device 200 comprises an electric motor 205 which is attached to fist plate 151 via a mounting plate 210. A screw drive 215 is engaged to electric motor 205 and a drive plate 218. Drive plate 218 is connected to a first pair of drive rods 220 and to a second pair of drive rods 225. First pair drive of rods 220 slidably enters end cap 149 while second pair of drive rods 225 slidably enters end cap 164.

Figure 3:
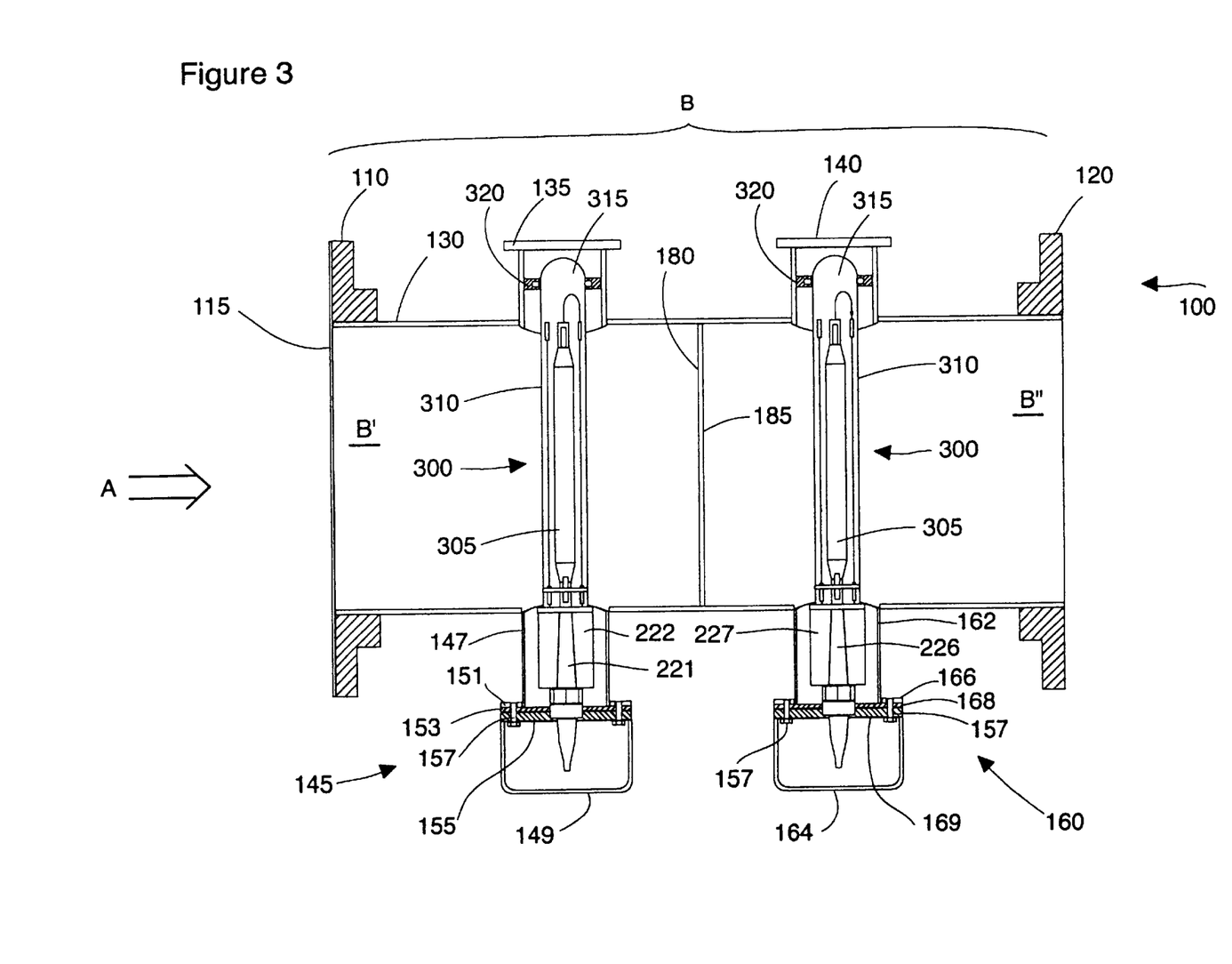
FIG. 3 illustrates a sectional view along line III—III in FIG. 1.
Figure 5:
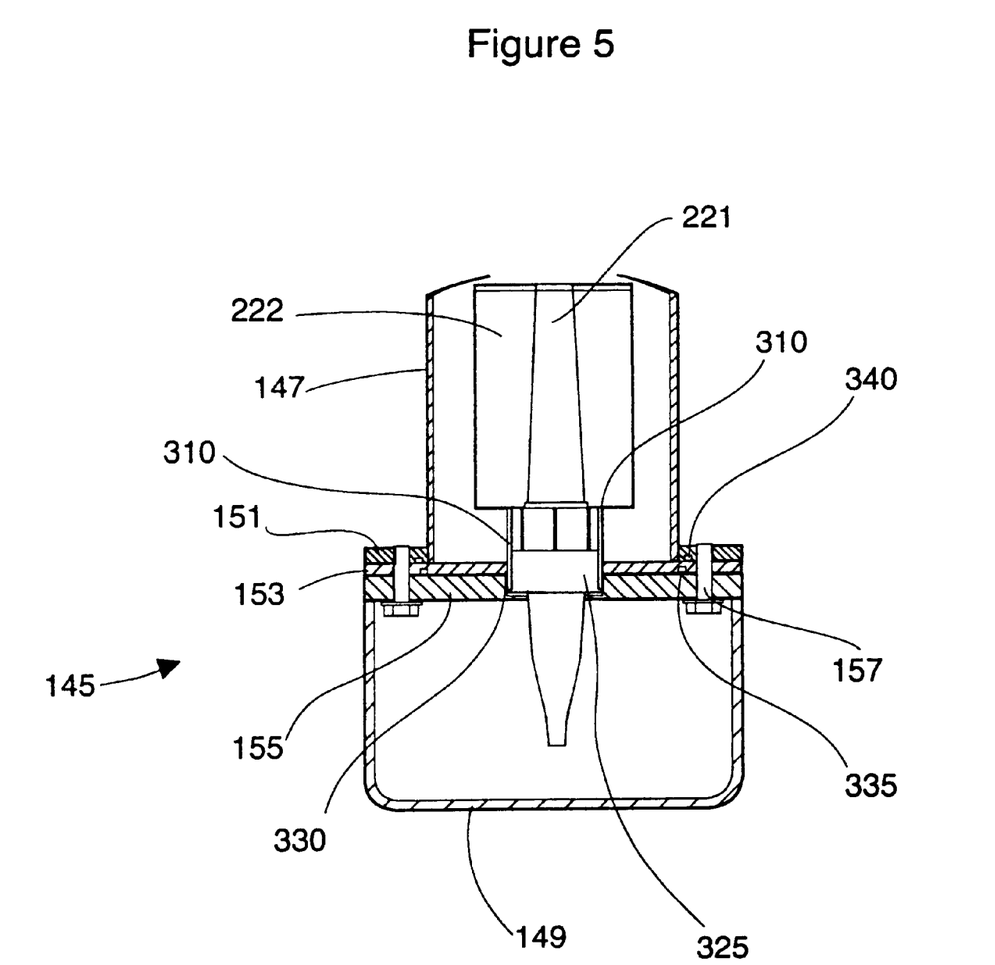
FIG. 5 illustrates an enlarged view of a portion of FIG. 3.

Drive rods 220 are connected to a pair of diametrically opposed sockets 221 (only one of the sockets is shown in FIGS. 3 and 5). Sockets 221 are threaded (not shown) and receive a complementary threaded end section (not show) of each drive rod 220. Sockets 221 are disposed on a cleaning sleeve 222. The design of cleaning sleeve 222 preferably is as set out in one or both of co-pending patent applications Ser. No. 60/136,766 (Dall'Armi et al.), filed on May 28, 1999, and Ser. No. 60/148,648 (Fang et al.), filed on Aug. 13, 1999.

Similarly, drive rods 225 are connected to a pair of diametrically opposed sockets 226 (only one of the sockets is shown in FIGS. 3 and 5). Sockets 226 are threaded (not shown) and receive a complementary threaded end section (not shown) of each drive rod 225. Sockets 226 are disposed on a cleaning sleeve 227. Again, the design of cleaning sleeve 227 preferably is as set out in one or both of co-pending patent applications Ser. No. 60/136,766 (Dall'Armi et al.), filed on May 28, 1999, and Ser. No. 60/148,648 (Fang et al.), filed on Aug. 13, 1999.

Disposed in housing 130 are a pair of radiation source assemblies 300. Each radiation source assembly 300 comprises a radiation source 305 contained within a protective sleeve 310. Preferably, each radiation source is a medium pressure ultraviolet radiation lamp. Such a lamps is conventional and commercially available from a number of suppliers. Preferably, the protective sleeve 310 is made of quartz or some other radiation transparent material. Protective sleeve 310 has a closed end 315 disposed in recesses 135,140 as appropriate. Closed end 315 of protective sleeve 310 is held in place by a suitable spacer arrangement 320.

The opposite end of protective sleeve 310 is open and abuts against a stop 325, preferably made from a polymer material such as rubber, plastic and the like. Protective sleeve 310 is sealed with respect to the exterior of tubular section 147 and 162 by an O-ring 330 which is disposed between second plate 153 and a third plate 155. Additionally, a second O-ring 335 is disposed between second plate 153 and third plate 155 and a third 0-ring 340 is place between first plate 151 and second plate 153. A series of threaded bolts 157 (only a pair are illustrated) are disposed in suitably threaded openings in plates 151,153, 155. When bolts 157 are tightened, the compression of plates 151,153,155 results in compression of O-rings 330,335, 340 resulting in the creation of a fluid tight seal with respect to the interior of housing 130 and the exterior of recess 145. With reference to FIG. 3, as bolts 157 are tightened, the compression of plates 166,168,169 results in compression of O-rings (not shown but similar to O-ring arrangement shown in FIG. 5) resulting in the creation of a fluid tight seal with respect to the interior of housing 130 and the exterior of recess 160.

Figure 4:
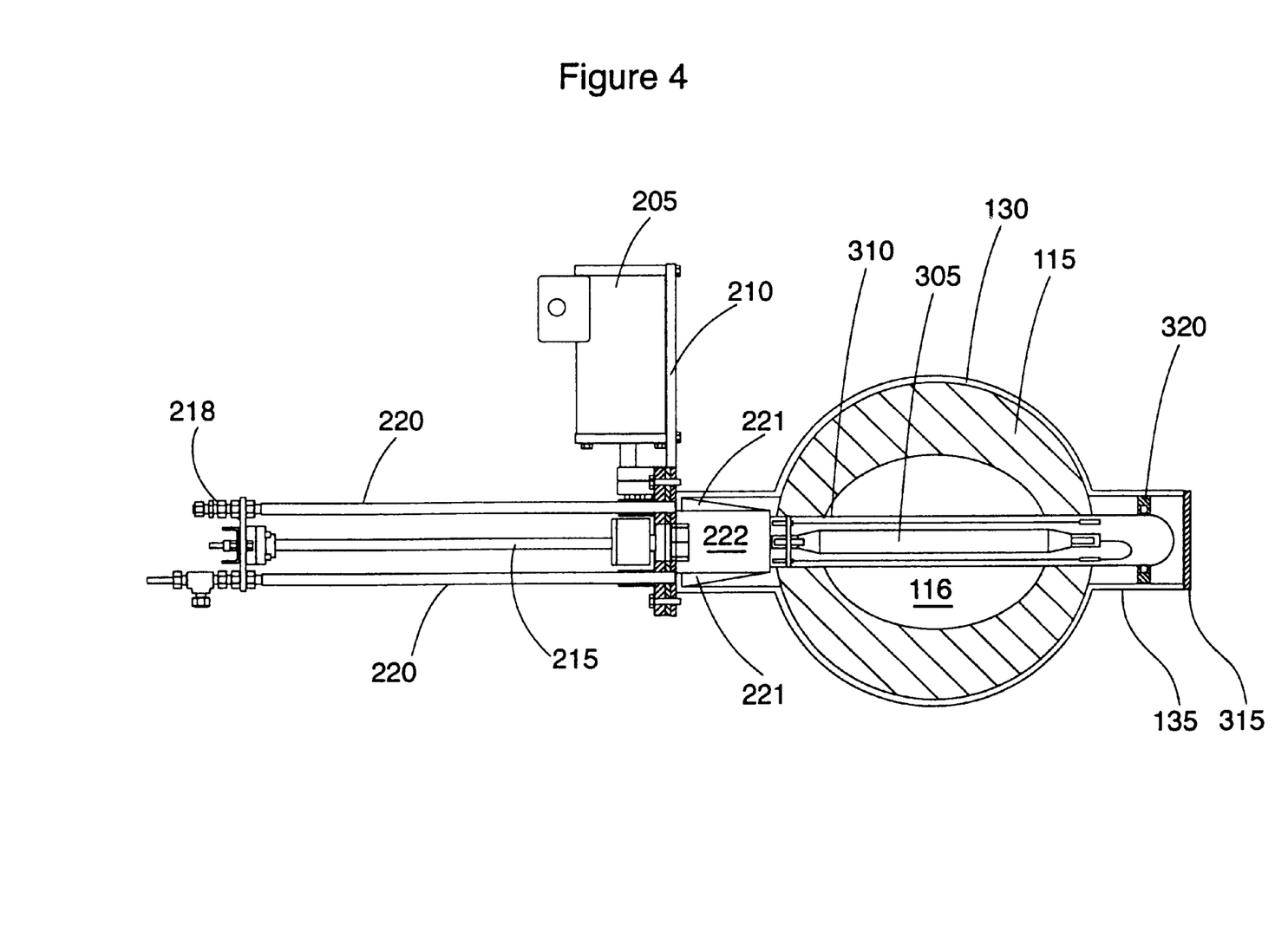
FIG. 4 illustrates a sectional view along line IV—IV in FIG. 1.

With reference to FIG. 3, a supplementary baffle plate 180 is interposed between pair of radiation source assemblies 300. Supplementary baffle plate 180 comprises an opening 185. With reference to FIG. 4, it will be seen that inlet plate 115 has an opening 116 substantially in the shape of an ellipse having the largest dimension which is substantially parallel to radiation source 305 and radiation source assembly 300. While not specifically shown in FIG. 4, it is preferred that opening 185 and supplementary baffle plate 180 have the same shape, dimension and orientation as opening 116 and inlet plate 115.

With reference to FIG. 3, the disposition of radiation source assemblies 300 in the manner illustrated defines a fluid treatment zone indicated generally by B (i.e. a zone in which fluid being treated is exposed to ultraviolet radiation from radiation sources 305). As illustrated, fluid treatment zone B comprises sub-zones B' and B" which are generally physically divided by supplementary baffle plate 180.

Figure 2:
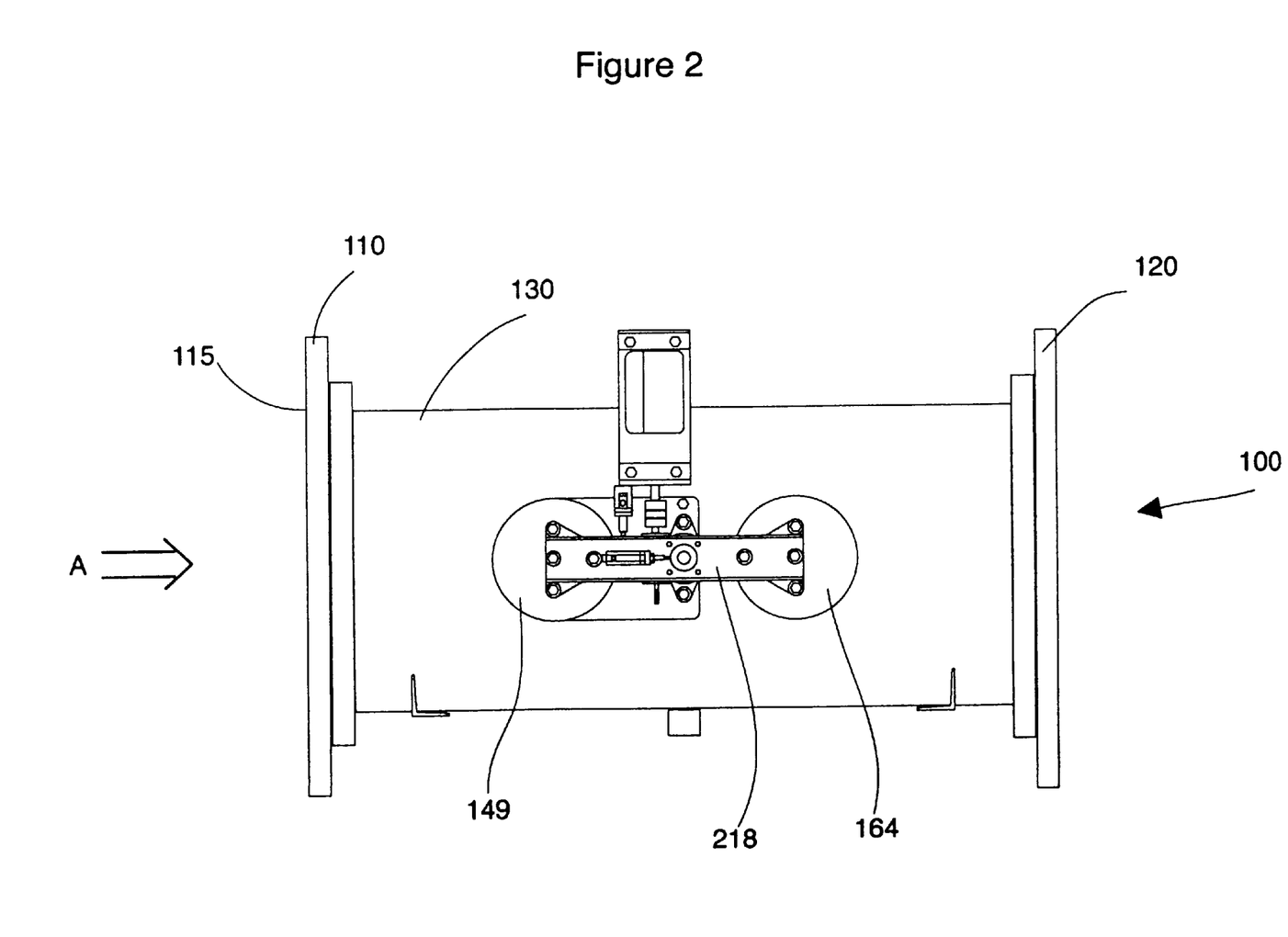
FIG. 2 illustrates a side elevation of the fluid treatment device illustrated in FIG. 1.

In use, inlet flange 110 is connected to a suitable supply pipe (not shown) and outlet flange 120 is connected to a suitable return supply pipe (not shown). Arrow A in FIGS. 1–3 illustrates the direction of fluid flow that enters housing 130. As the flow of fluid approaches inlet plate 115, it typically flows substantially parallel to the longitudinal axis of housing 130. The constriction offered by inlet plate 115 serves to: (i) cause mixing of the fluid flow as it enters fluid treatment zone B, and (ii) direct microorganisms contained in the fluid flow toward the radiation source(s) in the fluid treatment zone thereby obviating the microorganisms passing through fluid treatment zone B along the walls of housing 130. These features facilitate treatment of the fluid. Such treatment is further facilitated in fluid treatment zone B by the provision of supplementary baffle plate 180 having opening 185.

Ideally, fluid treatment device 100 is constructed to be used in-line in existing (e.g., water piping). Thus, for a given installation, it is desirable to design fluid treatment zone B such that it has substantially the same cross-sectional shape and dimension as the existing piping. Inlet flange 110 and outlet flange 120 can be used to facilitate installation of fluid treatment system 100 between mating flanges in the existing piping. Depending on the nature of fluid being treated and other factors, the exterior of protective sleeves 310 will become fouled with undesirable materials after a period of time. If these materials are not removed, the performance of fluid treatment device 100 suffers. Accordingly, cleaning device 200 may be periodically actuated to provide for in situ removal of the undesirable materials from the exterior of protective sleeves 310. Specifically, electric motor 205 may be actuated thereby rotating drive screw 215 which serves to extend drive rods 220,225 into end caps 149,164 respectively. This serves to extend cleaning sleeves 222,227 into fluid treatment zone B and over the fouled exterior of protective sleeves 310 thereby removing the fouling materials. The direction of screw drive 215 may then be reversed thereby withdrawing cleaning sleeves 220,227 over radiation sources 305 and into a parked position in tubular members 147,162, respectively. The design and operation of cleaning sleeves 222, 227 preferably is as set out in one or both of co-pending patent applications Ser. No. 60/136,766 (Dall'Armi et al.), filed on May 28, 1999, and Ser. No. 60/148,648 (Fang et al.), filed on Aug. 13, 1999.

Figure 6:
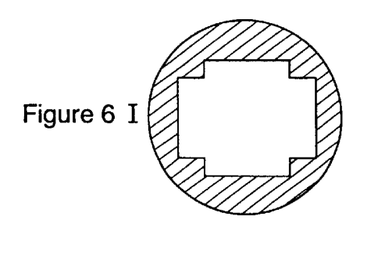
FIGS. 6a–6i illustrate various alternatives for an inlet baffle plate useful in the present fluid treatment device.
Figure 6A:
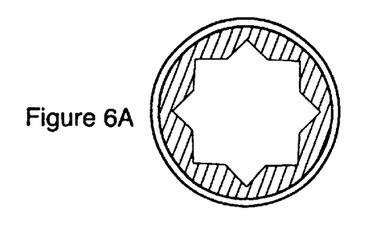
Figure 6B:
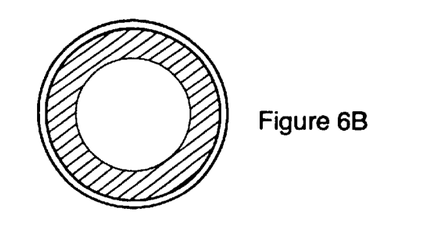
Figure 6C:
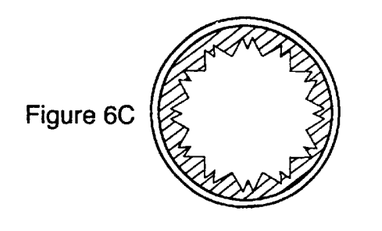
Figure 6D:
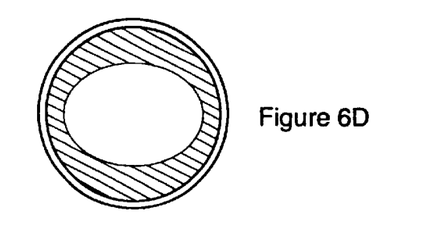
Figure 6E:
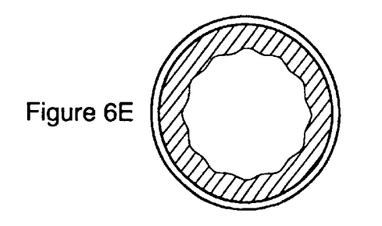
Figure 6F:
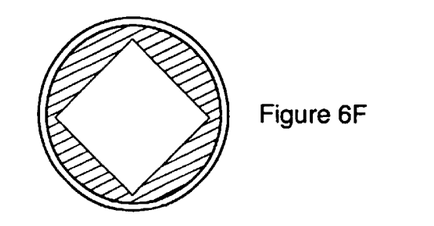
Figure 6G:
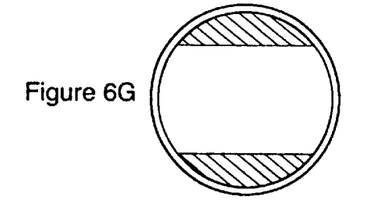
Figure 6H:
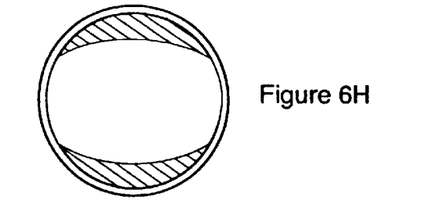

With reference to FIGS. 6a–6h there are illustrated various embodiments for the shape of the opening which may be used in inlet plate 115 and supplementary baffle plate 180. As shown, FIG. 6d is an illustration inlet plate 115 illustrated in FIGS. 1–4. FIGS. 6b,6c and 6e illustrates generally circular openings with the openings in FIGS. 6c and 6e having an undulating contour. The opening in FIG. 6f is square-shaped. The opening in FIG. 6g is obround-shaped. The opening in FIG. 6h is in the shape of a biconvex lens.

The opening in FIG. 6i is in the shape of a cruciform, which is a particularly preferred embodiment of the present invention. In the illustrated embodiment, the cruciform opening comprises a horizontal axis and a vertical axis. As shown and as is preferred, the horizontal axis is larger than the vertical axis. In the illustrated embodiment, the radiation source(s) would be disposed substantially parallel to the horizontal axis.

In a further aspect of the invention, it is preferred that the opening of the fluid inlet be configured such that the ends of the radiation source blocked thereby. More specifically, it is generally known in the art that a radiation source is of a given length has an arc length (i.e., the region of the source which actually emits radiation) which is less than the given length. In the present case its preferred to have the arc length of the radiation source to be substantially the same length as or greater than that of the largest diameter of the first opening. In this way, the portion of the radiation source which does not include the arc length (e.g., pinch end, electrical connections and the like) are "blocked" by the plate or other means used to provide the first opening (i.e., this may be appreciated by imaging the reverse view of FIG. 4).

Figure 7:
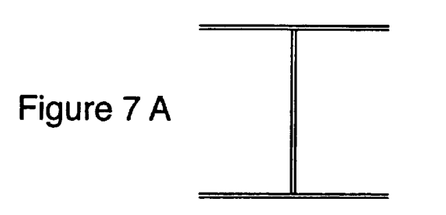
FIGS. 7a–7i illustrate various alternatives for the profile of an inlet baffle plate useful in the present fluid treatment device.

FIGS. 7a–7i illustrate various embodiments of the profile of the inlet plate, the supplementary baffle plate (if present) and the outlet plate (if present) which may be used with a fluid treatment device such as the one illustrated in FIGS. 1–4. Thus, as will be apparent to those of skill in the art, FIG. 7a illustrates the plate substantially transverse to the flow of water which is depicted by arrow A. The profile of the plate shown in FIG. 7b may be used with the shape of openings illustrated in FIGS. 6a, 6c and 6e. The profile in FIG. 7c is curved with respect to the direction of fluid flow through the device whereas the profile of the plate in FIG. 7b is angled with respect to the direction of fluid flow through the device. The profile of the plate in FIG. 7e is sinusoidal. In FIGS. 7g and 7h, there is illustrated an alternative to using a flat plate such as illustrated in FIGS. 7a–7f Specifically, in FIGS. 7g and 7h, a ridge is disposed on the outer walls of the housing to define an opening having a smaller cross sectional area than the cross sectional area of the fluid treatment zone.

While the present invention has been described with reference to preferred and specifically illustrated embodiments, it will of course be understood by those skilled in the arts that various modifications to these preferred and illustrated embodiments may be made without the parting from the spirit and scope of the invention. For example, it is possible to have different shaped openings at the inlet and outlet of the fluid treatment device provided at least the inlet has an opening with a cross sectional area less than the cross sectional area of the fluid treatment zone and has a largest diameter substantially parallel to the longitudinal axis of the radiation source assembly. Further, it is possible for the opening at either of the inlet or outlet ends of the reactor to have polygonal shape (e.g. rectangular, pentagonal, hexagonal, octagonal and the like). Further, it is possible for one or both of the openings at the inlet and outlet ends of the reactor to have plano-convex lens shape. Further, while the illustrated embodiment has been shown to include a generally cylindrical housing in which the fluid treatment zone is disposed, it is possible for the cross-sectional shape of the fluid treatment zone to be other than circular (e.g. polygonal, contoured and the like). Still further, while the illustrate embodiments utilize a single inlet/baffle plate upstream of each radiation source, it is possible to utilize more than a single baffle plate per radiation source and to place such baffle plate(s) in closer proximity to the radiation source(s). Still further, it is possible to utilize two or more radiation sources wherein the longitudinal axis of respective radiation sources are oblique with respect to one another. In this embodiment, it is possible (and preferred) to include at least one inlet/baffle plate upstream of each radiation source, the inlet/baffle plate having an opening with a largest diameter substantially parallel to the longitudinal axis of the radiation source directly downstream of the inlet/baffle plate. Still further, it is possible to use other types of cleaning systems with the present fluid treatment device (e.g. mechanical brushes and the like). Other modifications which do not depart from the spirit and scope of the present invention will be apparent to those skilled in the art.

All publications, patents and patent applications referred to herein are incorporated by reference in their entirety to the same extent as if each individual publication, patent or patent application was specifically and individually indicated to be incorporated by reference in its entirety.

What is claimed is:

1. A fluid treatment device comprising:
    a housing for receiving a flow of fluid, the housing comprising a fluid inlet, a fluid outlet, a fluid treatment zone disposed between the fluid inlet and the fluid outlet, and at least one radiation source having a longitudinal axis disposed in the fluid treatment zone substantially transverse to a direction of the flow of fluid through the housing;
    the fluid inlet, the fluid outlet and the fluid treatment zone arranged substantially co-linearly with respect to one another;
    the fluid inlet comprising a first opening having: (i) a cross-sectional area less than a cross-sectional area of the fluid treatment zone, and (ii) a largest diameter substantially parallel to the longitudinal axis of the at least one radiation source, said largest diameter being less than a diameter of the fluid treatment zone.

2. The fluid treatment device defined in claim 1, wherein the fluid treatment zone comprises at least two radiation sources, a supplementary baffle plate disposed downstream of a first radiation source, the supplementary baffle plate comprising a second opening having: (i) a cross-sectional area less than a cross-sectional area of the fluid treatment zone, and (ii) a largest diameter substantially parallel to the longitudinal axis of the at least one radiation source.

3. The fluid treatment device defined in claim 2, wherein first opening and the second opening have substantially the same cross-sectional area.

4. The fluid treatment device defined in claim 2, wherein the largest diameter of the first opening is substantially parallel to the largest diameter of the fluid second opening.

5. The fluid treatment device defined in claim 2, wherein the second opening comprises a substantially circular shape.

6. The fluid treatment device defined in claim 2, wherein the second opening comprises a substantially ellipsoidal shape.

7. The fluid treatment device defined in claim 2, wherein the second opening comprises an obroundal shape.

8. The fluid treatment device defined in claim 2, wherein the second opening comprises a polygonal shape.

9. The fluid treatment device defined in claim 2, wherein the second opening comprises a rectangular shape.

10. The fluid treatment device defined in claim 2, wherein the second opening comprises a square shape.

11. The fluid treatment device defined in claim 2, wherein the second opening comprises a pentagonal shape.

12. The fluid treatment device defined in claim 2, wherein the second opening comprises an octagonal shape.

13. The fluid treatment device defined in claim 2, wherein the second opening comprises a hexagonal shape.

14. The fluid treatment device defined in claim 2, wherein the second opening comprises a plano-convex lens shape.

15. The fluid treatment device defined in claim 2, wherein the second opening comprises a biconvex lens shape.

16. The fluid treatment device defined in claim 2, wherein the second opening comprises a cruciform shape.

17. The fluid treatment device defined in claim 16, wherein the cruciform shape comprises a first axis and a second axis orthogonal to the first axis.

18. The fluid treatment device defined in claim 17, wherein the the first axis and the second axis are of different length.

19. The fluid treatment device defined in claim 1, wherein the first opening comprises a substantially non-circular shape.

20. The fluid treatment device defined in claim 1, wherein the first opening comprises a substantially ellipsoidal shape.

21. The fluid treatment device defined in claim 1, wherein the first opening comprises an obroundal shape.

22. The fluid treatment device defined in claim 1, wherein the first opening comprises a polygonal shape.

23. The fluid treatment device defined in claim 1, wherein the first opening comprises a rectangular shape.

24. The fluid treatment device defined in claim 1, wherein the first opening comprises a square shape.

25. The fluid treatment device defined in claim 1, wherein the first opening comprises a pentagonal shape.

26. The fluid treatment device defined in claim 1, wherein the first opening comprises a hexagonal shape.

27. The fluid treatment device defined in claim 1, wherein the first opening comprises a octagonal shape.

28. The fluid treatment device defined in claim 1, wherein the first opening comprises a cruciform shape.

29. The fluid treatment device defined in claim 28, wherein the cruciform shape comprises a first axis and a second axis orthogonal to the first axis.

30. The fluid treatment device defined in claim 29, wherein the cruciform shape comprises the first axis and the second axis are of different length.

31. The fluid treatment device defined in claim 1, wherein the first opening comprises a plano-convex lens shape.

32. The fluid treatment device defined in claim 1, wherein the first opening comprises a biconvex lens shape.

33. The fluid treatment device defined in claim 1, wherein the housing comprises a substantially elongate cylinder.

34. The fluid treatment device defined in claim 1, wherein the housing comprises a substantially circular cross-section.

35. The fluid treatment device defined in claim 1, wherein the at least one radiation source comprises at least one ultraviolet lamp.

36. The fluid treatment device defined in claim 1, wherein the at least one radiation source further comprises a sleeve disposed about a portion of the exterior of the at least one ultraviolet lamp.

37. The fluid treatment device defined in claim 36, wherein the sleeve comprises a quartz sleeve.

38. The fluid treatment device defined in claim 1, further comprising a cleaning device to remove undesired materials from the exterior of the at least one radiation source.

39. The fluid treatment device defined in claim 38, wherein the cleaning device comprises a mechanical brush.

40. The fluid treatment device defined in claim 38, wherein the cleaning device comprises a wiper.

41. The fluid treatment device defined in claim 38, wherein the cleaning device comprises a cleaning sleeve for movement along an exterior of the at least one radiation source.

42. The fluid treatment device defined in claim 41, wherein the cleaning device further comprises motor causing movement of the cleaning sleeve.

43. The fluid treatment device defined in claim 42, wherein motor comprises an electric drive.

44. The fluid treatment device defined in claim 42, wherein motor comprises a hydraulic drive.

45. The fluid treatment device defined in claim 42, wherein motor comprises a pneumatic drive.

46. The fluid treatment device defined in claim 38, wherein the cleaning device comprises a cleaning sleeve for movement along an exterior of the at least one radiation source between a first cleaning position in which the cleaning sleeve at least partially covers the at least one radiation source and a second parked position in which the at least one radiation source is fully exposed with respect the cleaning sleeve.

47. The fluid treatment device defined in claim 46, wherein the cleaning sleeve comprises a chamber for receiving a cleaning fluid.

48. The fluid treatment device defined in claim 47, wherein the chamber is substantially sealed with respect to the exterior of the at least one radiation source.

49. The fluid treatment device defined in claim 47, wherein the chamber comprises at least one port to permit introduction to and withdrawal from the chamber of a cleaning fluid.

50. The fluid treatment device defined in claim 38, wherein the cleaning device comprises a scraper.

51. The fluid treatment device defined in claim 50, wherein the scraper comprises a cellular material.

52. The fluid treatment device defined in claim 1, further comprising means to monitor the level of radiation being emitted from the at least one radiation source.

53. A fluid treatment device comprising:
   a housing for receiving a flow of fluid, the housing comprising a fluid inlet, a fluid outlet, a fluid treatment zone disposed between the fluid inlet and the fluid outlet, and at least one radiation source having an arc length and a longitudinal axis disposed in the fluid treatment zone substantially transverse to a direction of the flow of fluid through the housing;
   the fluid inlet, the fluid outlet and the fluid treatment zone arranged substantially co-linearly with respect to one another;
   the fluid inlet comprising a first opening having: (i) a cross-sectional area less than a cross-sectional area of the fluid treatment zone, and (ii) a diameter less than the arc length of the at least one radiation source, said fluid inlet having at least one major axis and at least one minor axis, said major axis being less than a width of the fluid treatment zone.

54. Apparatus to constrain fluid flow in an radiation reactor having a radiation device with a longitudinal axis, comprising:
   baffle structure disposed on an upstream side of the radiation reactor, said baffle structure having a non-circular opening with a first axis and a second axis, each of said first axis and said second axis being smaller than an inside dimension of the radiation reactor, said first axis being substantially parallel to the longitudinal axis of the radiation device.

55. Apparatus according to claim 54, wherein said baffle structure comprises an elliptical opening having a major axis substantially parallel to the longitudinal axis of the radiation device.

56. Apparatus according to claim 54, wherein said baffle structure comprises a cruciform opening having one axis substantially parallel to the longitudinal axis of the radiation device.

* * * * *